(12) United States Patent
Alderson

(10) Patent No.: US 11,129,385 B2
(45) Date of Patent: Sep. 28, 2021

(54) C3-C5 N-ALKYL-GAMMA-BUTYROLACTAM-CONTAINING ANTIMICROBIAL COMPOSITIONS AND USES THEREOF

(71) Applicant: Randall Pilon, Oakville (CA)

(72) Inventor: Faraz A. Alderson, Oakville (CA)

(73) Assignee: VIROX TECHNOLOGIES INC., Oakville (CA)

( * ) Notice: Subject to any disclaimer, the term of this patent is extended or adjusted under 35 U.S.C. 154(b) by 0 days.

(21) Appl. No.: 16/830,539

(22) Filed: Mar. 26, 2020

(65) Prior Publication Data
US 2020/0236934 A1    Jul. 30, 2020

Related U.S. Application Data

(63) Continuation of application No. PCT/CA2019/051740, filed on Dec. 4, 2019.

(60) Provisional application No. 62/774,964, filed on Dec. 4, 2018.

(51) Int. Cl.
*A01N 43/36* (2006.01)
*A01N 25/30* (2006.01)

(52) U.S. Cl.
CPC .............. *A01N 43/36* (2013.01); *A01N 25/30* (2013.01)

(58) Field of Classification Search
CPC ..................................................... A01N 43/36
See application file for complete search history.

(56) References Cited

U.S. PATENT DOCUMENTS

| | | |
|---|---|---|
| 4,132,781 A | 1/1979 | Stoughton |
| 4,305,749 A | 12/1981 | Mildenberger et al. |
| 4,782,078 A | 11/1988 | Crawford et al. |
| 4,885,371 A | 12/1989 | Tracy et al. |
| 5,130,124 A | 7/1992 | Merianos et al. |
| 5,422,073 A | 6/1995 | Mowrey-McKee et al. |
| 5,972,237 A | 10/1999 | Muller et al. |
| 6,017,863 A | 1/2000 | Cala et al. |
| 6,100,227 A | 8/2000 | Burlew |
| 6,828,277 B2 | 12/2004 | Manzer |
| 7,419,944 B2 | 9/2008 | Mowrey-McKee et al. |
| 7,485,619 B2 | 2/2009 | Kim et al. |
| 7,666,823 B2 | 2/2010 | Minick |
| 8,268,763 B2 | 9/2012 | Lane et al. |
| 9,167,812 B2 * | 10/2015 | Bigorra Llosas ...... A01N 33/22 |
| 2004/0192933 A1 | 9/2004 | Manzer et al. |
| 2007/0270612 A1 | 11/2007 | Pompeo et al. |
| 2008/0095863 A1 | 4/2008 | Kabra |
| 2018/0002645 A1 | 1/2018 | Bartley et al. |
| 2018/0055048 A1* | 3/2018 | Premachandran ..... A01N 25/02 |
| 2019/0330489 A1* | 10/2019 | Dukhopelnikov ... C09D 139/06 |

FOREIGN PATENT DOCUMENTS

| | | | |
|---|---|---|---|
| CA | 2007239 A1 | | 7/1990 |
| GB | 1525120 A | | 9/1978 |
| JP | 73003394 | * | 1/1973 |
| JP | 2007-031299 A | | 2/2007 |
| WO | WO-95/21238 A1 | | 8/1995 |
| WO | WO-1996/02624 A1 | | 2/1996 |
| WO | WO-2002/50225 A1 | | 6/2002 |
| WO | WO-2002/50241 A2 | | 6/2002 |
| WO | WO-2003/006046 A1 | | 1/2003 |
| WO | WO-2003/094920 A1 | | 11/2003 |
| WO | WO-2004/074417 A1 | | 9/2004 |
| WO | WO-2006/005551 A1 | | 1/2006 |
| WO | WO2008/031104 | * | 3/2008 |
| WO | WO-2011/146182 A1 | | 11/2011 |
| WO | WO2013/107822 | * | 1/2013 |

OTHER PUBLICATIONS

Gaonkar et al. (In Vivo Efficacy of an Alcohol-based Surgical Hand Disinfectant Containing a Synergistic Combination of Ethylhexylglycerin and Preservatives). (Year: 2006).*
Search Report and International Application in International Application No. PCT/IB2019/059671 dated Jan. 14, 2020, 8 pages.
Dhavan et al., "Antibacterial and Antifungal Activities of 2,3-pyrrolidinedione Derivatives Against Oral Pathogens", Bioorganic and Medicinal Chemistry Letters, vol. 26(5), Feb. 4, 2016, 11 pages.
Zeng et al., "Antifungal Activities of (E)-4-benzylidene-5-oxopyrrolidine-2-carboxamides and 6-oxo-1,2,3,6-tetrahydropyridin-2-carboxamides Synthezed via Ugi Reaction From Baylis-hillman Bromides", 2nd International Conference on Agricultural and Biological Sciences (ABS 2016): IOP Conference Series: Earth and Environmental Science, vol. 41, 2016, pp. 1-5.
Hosseinzadeh et al., "An Overview on Chemistry and Biological Importance of Pyrrolidinone", Current Organic Synthesis, vol. 14, 2017, 14 pages.

(Continued)

*Primary Examiner* — Sarah Alawadi
(74) *Attorney, Agent, or Firm* — Marshall, Gerstein & Borun LLP

(57) ABSTRACT

An antimicrobial composition containing a diluent (e.g. water) and about 0.01 wt. % to about 90 wt. % of at least one compound according to Formula 1

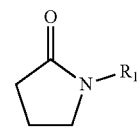

[Formula 1]

wherein $R_1$ is a branched or unbranched, saturated or unsaturated, C3 to C5 N-alkyl-chain and the antimicrobial composition is substantially free of peroxygen compounds, antibiotics, and chloroacetamide. Methods of using the composition to reduce the microbial load on a surface are also provided, as is the use of the compound according to Formula 1 as an antimicrobial agent.

21 Claims, No Drawings

(56) References Cited

OTHER PUBLICATIONS

Cardinal Intellectual Property, Patent Search Report, Patentability Search, "Antimicrobial Compositions for Use in Sanitization, Disinfection and Sterilization of Various Surf", Oct. 24, 2018, 13 pages.
Search Report in International Application No. PCT/CA2019/051740 dated Jan. 31, 2020, 6 pages.
International Preliminary Report on Patentability in International Application No. PCT/CA2019/051740 dated Mar. 4, 2021, 41 pages.

* cited by examiner

C3-C5 N-ALKYL-GAMMA-BUTYROLACTAM-CONTAINING ANTIMICROBIAL COMPOSITIONS AND USES THEREOF

CROSS-REFERENCE TO RELATED APPLICATIONS

This application is a continuation of international application no. PCT/CA2019/051740 filed Dec. 4, 2019, which in turn claims the benefit of and priority from U.S. provisional application 62/774,964 filed on Dec. 4, 2018 under 35 U.S.C. 119(d), the entire respective contents of which are incorporated herein by reference.

FIELD OF THE DISCLOSURE

The present specification relates to antimicrobial compositions and methods of using same for sanitization, disinfection and/or sterilization.

BACKGROUND OF THE DISCLOSURE

There is an ongoing effort to develop antimicrobial compositions that are effective against microorganisms, low in toxicity to humans and other animals, and not harmful to the environment.

Some antimicrobial compositions employ organic solvents as antimicrobial agents. Examples of organic solvents with antimicrobial properties include alcohols such as methanol, ethanol, isopropanol, benzyl alcohol, phenoxyethanol, and 2-butoxyethanol; dibasic esters such as dimethyl succinate and diethyl adipate; and glycol ethers such as diethylene glycol monobutyl ether. Benefits of using these organic solvents are that they can enhance soil removal and evaporate to leave no antimicrobial active residues on the surface.

Despite the positive attributes of the known antimicrobial solvents, they can suffer from certain unfavored qualities such being highly flammable, toxicity to users, and unfavourable environmental impact. Some other disadvantages can include being highly volatile and malodorous. Some antimicrobial solvents have low solubility/miscibility in aqueous solutions and some others can cause damage to plastics, resins, or painted surfaces. Finally, they can possess a low spectrum of antimicrobial activity and be ineffective against harder-to-kill microorganisms such as mycobacteria.

Accordingly, there is a need for new, safe, and effective antimicrobial compositions that are free of at least one or more of the above disadvantages.

SUMMARY OF THE DISCLOSURE

Surprisingly, the inventor has found that a class of solvents, namely, C3-C5 N-alkyl-gamma-butyrolactams, can be used as an antimicrobial agent and can also be used to synergistically enhance the antimicrobial activity of solutions containing other antimicrobial agents. An example solvent is N-butyl-gamma butyrolactam where the alkyl group has four carbon atoms. Surprisingly, these compounds are also effective against hard-to-kill microbes such as mycobacteria.

Effective antimicrobial compositions can be made using these solvents without containing any peroxygen compounds (herein defined) as antimicrobial agents. Furthermore, the compositions provided herein avoid utilizing N-alkyl-gamma-butyrolactam in combination with agricultural plant and crop treatment agents, examples of which are compounds selected from the group consisting of alachlor, alpha-cypermethrin, difenoconazole, glyphosate, oxyfluorfen, pendimethalin, phenmedipham, propanil, propoxur, tebuconazole, triadimenol, and trifluralin. Not only are these agents unfit for use in surface disinfection, sanitization and sterilization, they also have very low aqueous solubility, pose various health hazards, and may be environmental pollutants.

Accordingly, a first aspect of the invention provides an antimicrobial composition comprising, consisting essentially of, or consisting of:

(i) an effective amount of an antimicrobial agent consisting of a compound according to Formula 1:

[Formula 1]

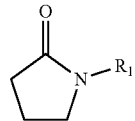

wherein $R^1$ is a branched or unbranched, saturated or unsaturated, C3 to C5 alkyl chain; and (ii) a diluent (e.g., water), q.s. to 100, wherein the composition is substantially free of peroxygen compounds, antibiotics, and chloroacetamide.

In certain embodiments, the at least one C3-C5 N-alkyl-gamma-butyrolactam is a C4 N-alkyl-gamma-butyrolactam. In the same or other embodiments, the N-alkyl-gamma-butyrolactam is selected from the group consisting of N-butyl-gamma-butyrolactam, N-isobutyl-gamma-butyrolactam, N-methoxypropyl-gamma-butyrolactam, and combinations thereof. In further embodiments, the N-alkyl-gamma-butyrolactam is N-butyl-gamma-butyrolactam.

The amount of diluent present will, together with other compounds that may be present in the composition, determine the concentration of the solvent C3-C5 N-alkyl-gamma-butyrolactam in solution. The more concentrated the solution, the more additional diluent that can be added by the end user prior to use. Thus, the present invention contemplates both ready-to-use (RTU) antimicrobial compositions as well as concentrated versions thereof.

The antimicrobial composition can further comprise at least one additional antimicrobial agent, such as an agent selected from the group consisting of carboxylic acids (e.g. linear carboxylic acids, cyclic carboxylic acids, mineral acids) and salts thereof, alcohols, anionic surfactants, amphoteric surfactants, quaternary ammonium compounds, phenols, aldehydes, biguanides, mineral acids, halogen compounds, glycerol ethers, other antimicrobial solvents, terpenes, essential oils, and antimicrobial metals. Examples of linear and cyclic carboxylic acids, without limitation, are citric acid, salicylic acid, 2-furoic acid, mandelic acid, glycolic acid, benzoic acid, acetic acid, dimethylol propionic acid, gallic acid, malic acid, lactic acid, sulfosuccinic acid, propionic acid, oxalic acid, and salts thereof.

In some embodiments, the antimicrobial compositions will contain antimicrobial agents selected from the group consisting of anionic surfactants, amphoteric surfactants, and quaternary ammonium compounds.

The antimicrobial composition can further comprise at least one ingredient selected from the group consisting of additional solvents, stabilizing agents, pH adjusting agents, buffering agents, nonionic surfactants, cationic surfactants, hydrotropes, skin conditioning agents, anti-foaming agents, builders, soil suspenders and anti-redeposition agents, brightening agents, radical scavengers, dyes, fragrances, rheology modifiers, emulsifiers, corrosion inhibitors, anti-foaming agents, softening agents, anti-static agents, anti-wrinkling agents, dye transfer inhibition/color protection agents, odor removal/odor capturing agents, preservatives, soil shielding/soil releasing agents, ultraviolet light protection agents, water repellency agents, insect repellency agents, anti-pilling agents, souring agents, mildew removing agents, film-forming agents, plasticizers, and allergicides.

According to a second aspect, the invention provides a new use of at least one C3-C5 N-alkyl-gamma-butyrolactam, according to Formula 1, as an antimicrobial agent, as well as a new use of at least one C3-C5 N-alkyl-gamma-butyrolactam to synergistically enhance the antimicrobial activity of an antimicrobial composition further comprising, consisting essentially of, or consisting of at least one additional antimicrobial agent, wherein the composition is substantially free of peroxygen compounds, antibiotics, and chloroacetamide. Some antimicrobially inert ingredients can also boost the antimicrobial efficacy of C3-C5 N-alkyl-gamma-butyrolactams. Examples of these antimicrobially inert ingredients include, without limitation, certain non-ionic surfactants, non-antimicrobial solvents, chelating agents, fatty acids, inorganic salts, hydrotropes, film forming agents, antioxidants, and emulsifiers. In certain embodiments, the at least one C3-C5 N-alkyl-gamma-butyrolactam is a C4 N-alkyl-gamma-butyrolactam. In certain embodiments, the N-alkyl-gamma-butyrolactam is selected from the group consisting of N-butyl-gamma-butyrolactam, N-isobutyl-gamma-butyrolactam, N-methoxypropyl-gamma-butyrolactam, and combinations thereof. In further embodiments, the N-alkyl-gamma-butyrolactam is N-butyl-gamma-butyrolactam.

A third aspect of the invention provides a method of reducing the microbial load on a surface contaminated with microbes, the method comprising (a) identifying a surface in need of microbial reduction; and (b) applying an antimicrobial composition comprising, consisting essentially of, or consisting of a composition, according to the first aspect, to the surface, for a time sufficient to reduce the microbial load by at least 50%. In certain embodiments, the at least one C3-C5 N-alkyl-gamma-butyrolactam is a C4 N-alkyl-gamma-butyrolactam. In the same or other embodiments, the N-alkyl-gamma-butyrolactam is selected from the group consisting of N-butyl-gamma-butyrolactam, N-isobutyl-gamma-butyrolactam, N-methoxypropyl-gamma-butyrolactam, and combinations thereof. In further embodiments, the N-alkyl-gamma-butyrolactam is N-butyl-gamma-butyrolactam. In some embodiments, the contact time for disinfection or sanitization can range from about 10 seconds to about 10 minutes, e.g. from about 10, 30, 45, or 60 seconds and up to about 10 minutes, 5 minutes, 4 minutes, 3 minutes, 2 minutes, or 1 minute. The microbes can be selected from the group consisting of bacteria, viruses, viroids, fungi, yeasts, mycobacteria, fungal spores, bacterial spores, phages, prions, protozoa, parasites, and combinations thereof. In some embodiments, the microbes include mycobacteria and/or bacteria. In certain embodiments, the method is performed at a temperature ranging from about −20° C. to about 80° C. and at an atmospheric pressure of from about 0 PSI to about 50 PSI units.

For the purpose of this disclosure, successful microbial reduction is achieved when the microbial populations are reduced by at least about 50% in 10 minutes. Larger reductions in microbial population will provide greater levels of protection. The level of protection required will depend on the application. In certain applications the antimicrobial composition may qualify as a sanitizer, disinfectant or sterilant, as defined herein.

Antimicrobial compositions consisting of, consisting essentially of, or comprising the at least one C3-C5 N-alkyl-gamma-butyrolactam can be used on surfaces such as hard and soft surfaces, including without limitation, skin, fur, instruments, machinery, apparatus, equipment, health care surfaces, food processing surfaces, plants, plant products, food products, meat products, poultry, poultry debris, wares, agricultural objects, veterinary objects, and soil. These compositions can be formulated into different formats, such as in the form of a clear solution or an emulsion, a gel, a foam, a cream, and a slurry, and can be applied using various machines, devices or articles such as, without limitation, a manually actuated trigger spray, aerosol canister, bag-on-valve canister, fogging device, misting device, foaming device, pre-moistened wipe substrate, mopping device, soaking container, ultrasonic bath, automated washing apparatus, ionizing spray, electrostatic spray, electrolyzing spray, steamer, and laundering machine.

The invention will now be described in further detail including with reference to examples.

DETAILED DESCRIPTION OF THE DISCLOSURE

For the sake of clarity and to avoid ambiguity, certain terms are defined herein as follows.

The term "comprising" means "including without limitation." Thus, a composition comprising a list of ingredients may include additional ingredients not expressly recited. The term "consisting of" means "including the listed ingredients and such additional ingredients as can be present in the listed ingredients as natural or commercial impurities or additives." Natural and commercial impurities and additives will be apparent to the person of ordinary skill in the art. The term "consisting essentially of" means "consisting of" the listed ingredients (as defined herein) and additional ingredients that would not "materially affect" the basic and novel properties of the composition." By "basic and novel properties" is meant the ability of the antimicrobial composition to reduce the microbial load on a surface contaminated with microbes. For the sake of clarity, a change in efficacy (positively or negatively) of greater than 0.3 log using ASTM E2197-02 test method against S. aureus, at a contact time of up to about 10 minutes, at 20-25° C., is deemed herein to constitute a "material effect." The term "weight percent," "wt. %," "percent by weight," "% by weight," % wt., and variations thereof, refer to the concentration of a substance as the weight of that substance divided by the total weight of the composition containing that substance, and multiplied by 100.

The term "about" refers to variations in an expressed numerical quantity that can occur, for example, through measuring and liquid handling procedures used for making concentrates or ready-to-use (RTU) solutions in the real world, differences in the manufacture, source, or purity of the ingredients used to make the compositions or carry out procedures, and differences due to different equilibrium conditions or different reaction levels for a composition resulting from an initial mixture. For the sake of clarity, the term "about" includes variations in the expressed value of ±5%. Whether a value is modified by the term "about," the specification includes equivalents to the values. Notwithstanding the foregoing, since pH is on a logarithmic scale, the term "about" when used to refer to pH means the expressed value ±0.5%.

When used herein, the term "effective amount" means an amount that would bring about a desired effect, based on the purpose and function of the ingredient and composition in which the ingredient is used. What constitutes an effective amount will be determinable by the person of ordinary skill in the art without having to engage in inventive experimentation. For example, an effective amount of a pH adjusting agent is that amount which would cause the pH of the solution to reach a desired value. An "effective amount" of an antimicrobial agent means an amount that, together with other ingredients in a composition will cause the composition to achieve the desired level of antimicrobial efficacy based on the intended application.

In the description and claims, the singular forms "a," "an," and "the" include plural referents unless the context clearly dictates otherwise. Thus, for example, reference to a composition containing "a compound" includes a composition having two or more compounds. It should also be noted that the term "or" is generally employed in the sense of "and/or" unless the context clearly dictates otherwise.

The ranges of values recited herein are intended to include all values within the ranges. Thus, for example, a range of 0.01 to 4.5 wt. % is intended to include values such as from 0.02, 0.03, or 0.04, etc. wt. % and up to 4.4, 4.3, or 4.2, etc. wt. %.

The term "microbial load" means the amount of microorganisms present on a surface to be disinfected. As used herein, the term "microorganism" refers to any non-cellular or unicellular (including colonial) organism. Microorganisms include bacteria (including cyanobacteria and mycobacteria), spores, lichens, fungi, protozoa, viruses, phages, prions, and some algae. As used herein, the term "microbe" is synonymous with microorganism.

As used herein, the phrase "food product" includes any food substance that might require treatment with an antimicrobial agent or composition and that is edible with or without further preparation. Food products include meat (e.g. red meat and pork), seafood, poultry, produce (e.g., fruits and vegetables), eggs, living eggs, egg products, ready to eat food, wheat, seeds, roots, tubers, leaves, stems, corns, flowers, sprouts, seasonings, or a combination thereof. The term "produce" refers to food products such as fruits and vegetables and plants or plant-derived materials that are typically sold uncooked and, often, unpackaged, and that can sometimes be eaten raw.

As used herein, the phrase "plant" or "plant product" includes any plant substance or plant-derived substance. Plant products include, but are not limited to, seeds, nuts, nut meats, cut flowers, plants or crops grown or stored in a greenhouse, house plants, and the like. Plant products include many animal feeds.

As used herein, the phrase "meat product" refers to all forms of animal flesh, including the carcass, muscle, fat, organs, skin, bones and body fluids and like components that form the animal. Animal flesh includes, but is not limited to, the flesh of mammals, birds, fishes, reptiles, amphibians, snails, clams, crustaceans, other edible species such as lobster, crab, etc., or other forms of seafood. The forms of animal flesh include, for example, the whole or part of animal flesh, alone or in combination with other ingredients. Typical forms include, for example, processed meats such as cured meats, sectioned and formed products, minced products, finely chopped products, ground meat and products including ground meat, whole products, and the like.

As used herein the term "poultry" refers to all forms of any bird kept, harvested, or domesticated for meat or eggs, and including chicken, turkey, ostrich, game hen, squab, guinea fowl, pheasant, quail, duck, goose, emu, or the like and the eggs of these birds. Poultry includes whole, sectioned, processed, cooked or raw poultry, and encompasses all forms of poultry flesh, by-products, and side products. The flesh of poultry includes muscle, fat, organs, skin, bones and body fluids and like components that form the animal. Forms of animal flesh include, for example, the whole or part of animal flesh, alone or in combination with other ingredients. Typical forms include, for example, processed poultry meat, such as cured poultry meat, sectioned and formed products, minced products, finely chopped products and whole products.

As used herein, the phrase "poultry debris" refers to any debris, residue, material, dirt, offal, poultry part, poultry waste, poultry viscera, poultry organ, fragments or combinations of such materials, and the like removed from a poultry carcass or portion during processing and that enters a waste stream.

As used herein, the phrase "food processing surface" refers to a surface of a tool, a machine, equipment, a structure, a building, or the like that is employed as part of a food processing, preparation, or storage activity. Examples of food processing surfaces include surfaces of food processing or preparation equipment (e.g., slicing, canning, or transport equipment, including flumes), of food processing wares (e.g., utensils, dishware, wash ware, and bar glasses), and of floors, walls, or fixtures of structures in which food processing occurs. Food processing surfaces are found and employed in food anti-spoilage air circulation systems, aseptic packaging sanitizing, food refrigeration and cooler cleaners and sanitizers, ware washing sanitizing, blancher cleaning and sanitizing, food packaging materials, cutting board additives, third-sink sanitizing, beverage chillers and warmers, meat chilling or scalding waters, auto dish sanitizers, sanitizing gels, cooling towers, food processing antimicrobial garment sprays, and non-to-low-aqueous food preparation lubricants, oils, and rinse additives.

As used herein, the term "ware" refers to items such as eating and cooking utensils, dishes, and other hard surfaces such as showers, sinks, toilets, bathtubs, countertops, windows, mirrors, transportation vehicles, and floors. Ware also refers to items made of plastic. Types of plastics that can be cleaned with the compositions according to the invention include but are not limited to, those that include polycarbonate polymers (PC), acrilonitrile-butadiene-styrene polymers (ABS), and polysulfone polymers (PS). Another exemplary plastic that can be cleaned using the compounds and compositions of the invention include polyethylene terephthalate (PET).

As used herein, the phrase "health care surface" refers to a surface of an instrument, a device, a cart, a cage, furniture, a structure, a building, or the like that is employed as part of a health care activity. Examples of health care surfaces include surfaces of medical or dental instruments, of medical or dental devices, of electronic apparatus employed for monitoring patient health, and of floors, walls, or fixtures of structures in which health care occurs. Health care surfaces are found in hospital, surgical, infirmity, birthing, mortuary, and clinical diagnosis rooms. These surfaces can be those typified as "hard surfaces" (such as walls, floors, bed-pans, etc.), or fabric surfaces, e.g., knit, woven, and non-woven surfaces (such as surgical garments, draperies, bed linens, bandages, etc.), or patient-care equipment (such as respirators, diagnostic equipment, shunts, body scopes, wheel chairs, beds, etc.), or surgical and diagnostic equipment. Health care surfaces include articles and surfaces employed in animal health care.

As used herein, the term "instrument" refers to the medical and dental instruments, devices, tools, appliances, apparatus, and equipment used in medicine or dentistry. Such instruments, devices, and equipment can be cold sterilized, soaked or washed and then heat sterilized, or otherwise benefit from cleaning in a composition of the present specification. These various instruments, devices and equipment include, but are not limited to: diagnostic instruments, trays, pans, holders, racks, forceps, scissors, shears, saws (e.g. bone saws and their blades), hemostats, knives, chisels, rongeurs, files, nippers, drills, drill bits, rasps, burrs, spreaders, breakers, elevators, clamps, needle holders, carriers, clips, hooks, gouges, curettes, retractors, straightener, punches, extractors, scoops, keratomes, spatulas, expressers, trocars, dilators, cages, glassware, tubing, catheters, cannulas, plugs, stents, scopes (e.g., endoscopes, stethoscopes, and arthroscopes) and related equipment, or any other devices that can benefit from treatment with an antimicrobial composition according to the present specification.

As used herein, "agricultural" or "veterinary" objects or surfaces include animal feeds, animal watering stations and enclosures, animal quarters, animal veterinarian clinics (e.g. surgical or treatment areas), animal surgical areas, and the like.

As used herein, the term "sanitizer" refers to an agent that reduces the number of bacterial contaminants to safe levels as judged by public health requirements. Sanitizers are defined herein as compositions that can provide at least a 99.9% reduction of live microbial cells (3-log order reduction). As used herein, the term "disinfectant" refers to an agent that reduces the number of bacterial contaminants to safer levels as judged by public health requirements. Disinfectants are defined herein to mean a composition that can provide at least a 99.999% reduction of live microbial cells (5-log order reduction). As used herein, the term "sterilant" refers to an agent that inactivates the entire microbial load on a given surface. These reductions can be evaluated using a variety of different antimicrobial efficacy testing methods, as required by specific regulatory agencies such as Unites States Environmental Protection Agency, Health Canada, and Biocidal Products Regulation of European Union.

As used herein, the term "q.s." means "quantum sufficit" or "quantum satis" a Latin term meaning the amount which is enough, or standard pharmaceutical meaning of "as much as is sufficient".

As used herein, the term "synergistic" or "synergy" refers to a result that is more than merely additive. For example, if 'Solution 1' containing 1% of antimicrobial Agent-A demonstrates a bacterial $\log_{10}$ reduction of 0.5, and 'Solution 2' containing 1% of antimicrobial Agent-B demonstrates a bacterial $\log_{10}$ reduction of 0.5, then 'Solution 3' containing 1% of each of Agent-A and Agent-B would only be synergistic if it demonstrates a bacterial $\log_{10}$ reduction of greater than 1.

As used herein, the term "alkyl" or "alkyl groups" refers to saturated hydrocarbons having one or more carbon atoms, including straight-chain alkyl groups (e.g., methyl, ethyl, propyl, butyl, pentyl, hexyl, heptyl, octyl, nonyl, decyl, etc.), cyclic alkyl groups (or "cycloalkyl" or "alicyclic" or "carbocyclic" groups) (e.g., cyclopropyl, cyclopentyl, cyclohexyl, cycloheptyl, cyclooctyl, etc.), branched-chain alkyl groups (e.g., isopropyl, tert-butyl, sec-butyl, isobutyl, etc.), and alkyl-substituted alkyl groups (e.g., alkyl-substituted cycloalkyl groups and cycloalkyl-substituted alkyl groups).

Unless otherwise specified, the term "alkyl" includes both "unsubstituted alkyls" and "substituted alkyls." As used herein, the term "substituted alkyls" refers to alkyl groups having substituents replacing one or more hydrogens on one or more carbons of the hydrocarbon backbone. Such substituents may include, for example, alkenyl, alkynyl, halogeno, hydroxyl, alkylcarbonyloxy, arylcarbonyloxy, alkoxycarbonyloxy, aryloxy, aryloxycarbonyloxy, carboxylate, alkylcarbonyl, arylcarbonyl, alkoxycarbonyl, aminocarbonyl, alkylaminocarbonyl, dialkylaminocarbonyl, alkylthiocarbonyl, alkoxyl, phosphate, phosphonate, phosphine, cyano, amino (including alkyl amino, dialkylamino, arylamino, diarylamino, and alkylarylamino), acylamino (including alkylcarbonylamino, arylcarbonylamino, carbamoyl and ureido), imino, sulfhydryl, alkylthio, arylthio, thiocarboxylate, sulfates, alkylsulfinyl, sulfonates, sulfamoyl, sulfonamido, nitro, trifluoromethyl, cyano, azido, heterocyclic, alkylaryl, or aromatic (including heteroaromatic) groups.

In some embodiments, substituted alkyls can include a heterocyclic group. As used herein, the term "heterocyclic group" includes closed ring structures analogous to carbocyclic groups in which one or more of the carbon atoms in the ring is an element other than carbon, for example, nitrogen, sulfur or oxygen. Heterocyclic groups can be saturated or unsaturated. Exemplary heterocyclic groups include, but are not limited to, aziridine, ethylene oxide (epoxides, oxiranes), thiirane (episulfides), dioxirane, azetidine, oxetane, thietane, dioxetane, dithietane, dithiete, azolidine, pyrrolidine, pyrroline, oxolane, dihydrofuran, and furan.

The chemical structures herein are drawn according to the conventional standards known in the art. Thus, where an atom, such as a carbon atom, as drawn appears to have an unsatisfied valency, then that valency is assumed to be satisfied by a hydrogen atom, even though that hydrogen atom is not necessarily explicitly drawn. The structures of some of the compounds of this invention include stereogenic carbon atoms. It is to be understood that isomers arising from such asymmetry (e.g., all enantiomers and diastereomers) are included within the scope of this invention unless indicated otherwise. That is, unless otherwise stipulated, any chiral carbon center can be of either (R) or (S) stereochemistry. Such isomers can be obtained in substantially pure form by classical separation techniques and by stereochemically-controlled synthesis. Furthermore, alkenes can include either the E- or Z-geometry, where appropriate. In addition, the compounds of the present specification may exist in unsolvated as well as solvated forms with acceptable solvents such as water, propylene glycol, ethanol, and the like. In general, the solvated forms are considered equivalent to the unsolvated forms for the purposes of the present specification.

The present specification contemplates the possibility of omitting any components listed herein. The present specification further contemplates the omission of any components even though they are not expressly named as included or excluded from the invention.

C3-C5 N-Alkyl-Gamma-Butyrolactams

The C3-C5 N-alkyl-gamma-butyrolactam family of compounds are represented by the following formula:

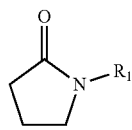

[Formula 1]

wherein $R_1$ is a branched or unbranched, saturated or unsaturated, unsubstituted C3-C5 alkyl chain or a C3 alkyl chain substituted with a methoxy group. These compounds include N-propyl-gamma-butyrolactam, N-isopropyl-gamma-butyrolactam, N-butyl-gamma-butyrolactam, N-pentyl-gamma-butyrolactam, and N-isopentyl-gamma-butyrolactam. Other variants of N-alkyl-gamma-butyrolactam can include, without limitation, N-isobutyl-gamma-butyrolactam, and N-methoxypropyl-gamma butyrolactam.

C3-C5 N-alkyl-gamma-butyrolactam compounds are known to be polar aprotic solvents possessing high chemical and thermal stability. They are normally used to provide solvency for a wide range of compounds. Other known uses include applications in specialty polymer coatings (wire enamels & coated cooking gear), micro-electronics manufacturing (photoresist stripper), other coatings (waterborne polyurethane dispersions), paint strippers and inks, chemical synthesis and agrochemical formulations. See, for example, US 2015/0057375 A1 to Vandeputte et al. which is incorporated herein by reference.

There is literature teaching the use of N-alkyl pyrrolidones in compositions for treating medical conditions or diseases. For example, U.S. Pat. No. 4,132,781, which is incorporated herein by reference, teaches a topical antibacterial composition and method for treatment of acne. The composition taught therein contains an antibiotic of the erythromycin family and 2-pyrrolidone or an N-lower alkyl-2-pyrrolidone. GB1525120, which is incorporated herein by reference, teaches topical antimicrobial compositions for the treatment of acne comprising 0.1 to 10% by weight of an antibiotic selected from griseofulvin and erythromycin or lincomycin together with 5 to 99.9% by weight of 2-pyrrolidone or an N-alkyl-2-pyrrolidone. As will be appreciated by a person of skill in the art, these references are directed to treatment of a medical condition and require the use of the antibiotics cited therein.

Surprisingly, the inventor has found that C3-C5 N-alkyl-gamma-butyrolactam compounds possess antimicrobial activity making them useful in antimicrobial compositions for reducing the microbial load on a surface contaminated with microbes. These compounds can be used "straight" (100 wt. % concentration) to reduce the microbial load on a surface, or combined with other ingredients, e.g. a diluent and/or additional ingredients to make an antimicrobial composition. Also surprisingly, the inventor has found that these compounds can synergistically enhance the antimicrobial activity of an antimicrobial composition that contains one or more additional antimicrobial agents. In such antimicrobial composition, specifically in a solution, the at least one C3-C5 N-alkyl-gamma-butyrolactam can be present in a concentration of from about 0.01, 0.1, 0.25, 0.5, 1, 2.5, 5, 7, 9 or 10 wt. % and up to about 99.9, 90, 85, 80, 75, 70, 65, 60, 55, 50, 45, 40, 35, 30, 25, 20, 18, 16, 14 or 12 wt. %. The solvent will generally not be more than about 15 wt. % in ready-to-use solutions, or less than about 4 wt. % in concentrated solutions. Concentrated versions of solutions containing at least one C3-C5 N-alkyl-gamma-butyrolactam can be diluted by the end user with water or another diluent. In certain embodiments, the concentrated version may be diluted, for example, at a ratio of 1:1, 1:4, 1:8, 1:16, 1:32, 1:64, 1:128, 1:256, or 1:512 (composition:diluent) or at other ratios in between these values; the amount of diluent required depends on the concentration of the C3-C5 N-alkyl-gamma-butyrolactam in overall antimicrobial composition. The present invention also contemplates a kit of parts wherein the at least one C3-C5 N-alkyl-gamma-butyrolactam is present as one part of the kit to be combined with other parts to form an antimicrobial composition prior to use.

C3-C5 N-alkyl-gamma-butyrolactam compounds, such as N-butyl-gamma-butyrolactam, possess a mild and agreeable odor and are not toxic to mammals, not highly volatile and are less flammable than their shorter-chained C1 and C2 versions. The C1 and C2 versions are known to be toxic to mammals and their use in the present antimicrobial compositions is to be avoided. Furthermore, the C3-C5 N-alkyl-gamma-butyrolactams, such as N-butyl-gamma-butyrolactam, are fully soluble in water and other aqueous solutions. In contrast, N-alkyl-gamma-butyrolactams with an alkyl chain length greater than C6 can have little to no solubility in water. The C3-C5 N-alkyl-gamma-butyrolactams are also more compatible with and safer to use on plastics, resins, and painted surfaces. In contrast, other antimicrobial solvents, such as benzyl alcohol, are incompatible for use on plastic and polymeric surfaces such as acrylics, acetals, and polyurethanes, though they may be effective against mycobacteria.

N-alkyl-gamma-butyrolactams with an alkyl chain length of greater than C6, e.g. C7 to C20 N-alkyl-gamma-butyrolactams such as octyl-gamma-butyrolactam (trade name: Surfadone™ LP-100), fall under the category of nonionic surfactants and are no longer considered to be solvents. C7 to C20 N-alkyl-gamma-butyrolactams have limited solubility in water due to the longer length of their alkyl chains and hence increased lipophilicity.

Peroxygen Compounds

The present compositions are substantially free of peroxygen compounds. When used herein, the term "substantially free" in relation to a compound means that the compound is not intentionally added to the composition. The skilled person will appreciate a compound may not be added and yet minute quantities may be present as impurities resulting from impurities in raw materials used to make the compositions or from reactions between and amongst ingredients in raw materials used to make the compositions. For the sake of clarity, the term "substantially free" in relation to a compound shall mean that the compound is present in an amount less than 0.1 wt. %.

When used herein, a "peroxygen compound" is a compound containing an oxygen-oxygen single bond or the peroxide anion. Examples include alkali metal peroxides (e.g. sodium peroxide). Also included are compounds that generate and release hydrogen peroxide when dissolved in aqueous solution (e.g. urea peroxide, perboric acid, sodium/potassium perborate, sodium persulfate, calcium peroxide, lithium peroxide, sodium peroxide, or other peroxides of alkali, alkaline earth, or transition group metals or salts thereof).

Still other examples are organic compounds containing two oxygens that are connected to each other through a single covalent bond, wherein the second chemical bond on each of the two oxygens attaches them, independently, to an organic moiety. The attached organic moieties can be independently a substituted or unsubstituted, branched or unbranched, saturated or unsaturated, cyclic or linear alkyl group. Examples include dialkyl peroxides such as dibenzoyl peroxide, diacetyl peroxide, di(n-propyl) peroxydicarbonate, butyl peroxybenzoate, and many others commercially available, without limitation, under the brand name Luperox™. In certain cases, at least one of the organic moieties can be sulfur or phosphorus atoms (e.g. peroxidisulfuric acid). In certain examples, one of the two attached organic moieties could be hydrogen. Examples of such molecules include, without limitation, hydrogen peroxide, butyl hydroperoxide, ethylidene peroxide, and ethyl hydroperoxide. In certain cases, at least one of the moieties can be sulfur or phosphorus atoms (e.g. peroximonosulfuric acid). Examples of peroxygen compounds expressly excluded from compositions according to the invention are hydrogen peroxide, sodium peroxide, benzoyl peroxide, dibenzyl peroxides, percarbonates (e.g. sodium percarbonates, potassium percarbonates), peroxymonosulfuric acid, and peroxydisulfuric acid.

Additional Ingredients

Depending on the application and properties that are desired for the antimicrobial composition, additional ingredients can be included such as at least one ingredient selected from the group consisting of chelating agents, pH adjusting agents, buffering agents, additional solvents, additional antimicrobial agents, nonionic surfactants, anionic surfactants, amphoteric surfactants, cationic surfactants, hydrotropes, skin conditioning agents, anti-foaming agents, builders, soil suspenders and anti-redeposition agents, brightening agents, radical scavengers, dyes, fragrances, rheology modifiers, corrosion inhibitors, softening agents, anti-static agents, anti-wrinkling agents, dye transfer inhibition/color protection agents, odor removal/odor capturing agents, preservatives, soil shielding/soil releasing agents, ultraviolet light protection agents, water repellency agents, insect repellency agents, anti-pilling agents, souring agents, mildew removing agents, film-forming agents, plasticizers, and allergicides.

Additional Antimicrobial Agent

In certain embodiments, the present compositions comprise at least one additional antimicrobial agent selected from the group consisting of inorganic or organic acids, alcohols, anionic surfactants, amphoteric surfactants, quaternary ammonium compounds, phenols, aldehydes, biguanides, terpenes, essential oils, mineral acids, halogen compounds, and antimicrobial metals such as copper, and mixtures thereof. Organic acids include mono or poly carboxylic acids, including linear and cyclic carboxylic acids.

When used, in certain embodiments, the concentration of the antimicrobial compound can be from about 0.005, 0.1, 1, 5, 10, or 20 wt. %, and up to about 60, 50, 40, 30, 25, 15, 8, 3, or 0.5 wt. %.

Carboxylic Acids

In some embodiments, the compositions comprise at least one cyclic or linear, branched or unbranched, saturated or unsaturated, substituted or unsubstituted, mono-, di- or poly-carboxylic acid or salt thereof. In certain embodiments the carboxylic acid or salt can be chosen from C1 to C22 carboxylic acids and salts. In some embodiments, the carboxylic acid or salt can be a C5 to C11 carboxylic acid or salt. In some embodiments, the carboxylic acid or salt can be a C1 to C4 carboxylic acid or salt. Examples of suitable carboxylic acids and salts thereof include but are not limited to 2-furoic acid, salicylic acid, benzoic acid, citric acid, sulfosalicylic acid, sulfosuccinic acid, glycolic acid, lactic acid, formic acid, oxalic acid, malic acid, acetic acid, propionic acid, butanoic acid, pentanoic acid, hexanoic acid, heptanoic acid, octanoic acid, nonanoic acid, decanoic acid, undecanoic acid, dodecanoic acid, as well as their branched isomers, maleic acid, ascorbic acid, alpha-or-beta hydroxyacetic acid, neopentanoic acid, neoheptanoic acid, neodecanoic acid, malonic acid, succinic acid, glutaric acid, adipic acid, pimelic acid, suberic acid, salts thereof and mixtures thereof. Some embodiments will have at least one acid and/or salt selected from the group consisting of salicylic acid, 2-furoic acid, benzoic acid, and salts thereof.

In certain embodiments, the acid and/or salt can be present in a concentration of from about 0.02, 0.05, 0.1, 0.5, or 1 wt. % and up to about 15, 13, 10, 8, 6, 4, or 3 wt. %. The acid and/or salt will generally not be higher than 8 wt. % in ready-to-use solutions, or lower than 1 wt. % in concentrated solutions.

Other Solvents

The present compositions can optionally contain at least one additional solvent to, for example, enhance cleaning and/or to help solubilize ingredients in the solution.

Exemplary additional solvents include cyclic alcohols (e.g. phenethyl alcohol, benzyl alcohol, phenoxyethanol, and cyclopentylmethanol), carbonates (e.g. ethylene carbonate, propylene carbonate, butylene carbonate, and glycerin carbonate), dimethyl succinate, benzyl acetate, benzyl benzoate, acetophenone, 2-acetyl-1-methylpyrrole, diester dicarboxylates (e.g., dibasic esters, such as dialkyl adipate, dialkyl glutarate, dialkyl succinate), dialkyl carbonate, organo-nitriles, phthalate esters, propylene glycol derivatives with ethoxylation and/or propoxylation, alkoxytriglycols and other glycols such as methoxytriglycol, ethoxytriglycol, butoxytriglycol, hexyltriglycol, propylene glycol methyl ether acetate, dipropylene glycol methyl ether acetate, dipropylene glycol n-butyl ether, propylene glycol n-butyl ether, dipropylene glycol n-propyl ether, propylene glycol n-propyl ether, dipropylene glycol methyl ether, tripropylene glycol methyl ether, methanol, ethanol, butyl 3-hydroxybutyrate, isopropyl alcohol, ethylhexylglycerol, branched or unbranched diols, charged or uncharged non-surfactant emulsifying agents, polar protic solvents, polar aprotic solvents, diethylene glycol monobutyl ether, diethylene glycol monoethyl ether, $C_1$-$C_8$ alcohols (e.g. methanol, ethanol, propanol, butanol, etc.) and mixtures thereof.

In certain embodiments the additional solvent(s) is present in a concentration of from about 0.01, 0.5, 1, 2.5, 5, 7, 9 or 10 wt. % and up to about 50, 40, 30, 20, 18, 16, or 14 wt. %. The additional solvent(s) will generally not be more than about 20 wt. % in ready-to-use solutions, or more than about 50 wt. % in concentrated solutions.

Chelating Agents

Chelating agents can be included for the purpose of metal ion chelation, corrosion prevention, and in certain cases as antimicrobial agents or enhancers. These include, without limitation, 1-hydroxyethane-1,1-diphosphonic acid (HEDP, also referred to herein as etidronic acid), ethylenediaminetetraacetic acid (EDTA), glutamic acid diacetic acid (GLDA), methylglycine diacetic acid (MGDA), polymandelic acid, diethylenetriaminepentaacetic acid (DTPA), N-(hydroxyethyl)-ethylenediaminetriacetic acid (HEDTA), nitrilotriacetic acid (NTA), 2-hydroxyethyliminodiacetic acid (HEIDA), benzoic acid, aminobenzoic acid, citric acid, iminodisuccinic acid, polyaspartic acid, phosphoric acid, tripolyphosphate, amino tri(methylene phosphonic acid) (ATMP), diethylenetriaminepenta(methylene phosphonic acid), 2-hydroxy ethylimino bis(methylene phosphonic acid), ethylene diamine tetra(methylene phosphonic acid), hexamethylenediamine-tetra(methylene phosphonic) acid, and salts thereof.

When used, in certain embodiments, the chelating agents can be present in a concentration of from about 0.005, 0.1, 1, 2, 3, 4, 5, 7, or 10 wt. % and up to about 20, 17.5, 15, 12.5, 8.5, or 2.5 wt. %.

pH Adjusting and Buffering Agents

In aqueous antimicrobial compositions, at least one pH adjusting agent and/or buffering agent can be used in an amount effective to adjust and/or keep the pH of the solution to within the desired pH range. Examples include, without limitation, inorganic acids (e.g. phosphoric acid) and salts thereof, organic acids (e.g. citric acid, methane sulfonic acid, p-toluene sulfonic acid) and salts thereof, and alkaline agents (e.g. potassium hydroxide and sodium hydroxide).

The desired pH will depend on the specific application as will be apparent to the skilled person. For example, if an additional antimicrobial agent is used, the desired pH may be the value or range of values at which the additional antimicrobial agent is most effective, or to provide specific desired properties. This pH will vary from agent to agent and will be known to the skilled person having regard to information in the public domain. Therefore, aqueous compositions can have a pH ranging from 0 to 14.

In ready-to-use or concentrated embodiments, in certain embodiments, the pH can range from about 0.1, 1, 1.5, 2, 2.5, 3, 3.5, 4, 4.5, 5, 5.5, 6, 6.5, 7, 7.5, or 8, and up to about 12, 11.5, 11, 10.5, 10, 9.5, 9, or 8.5. In concentrated solutions, in certain embodiments, the pH can range from about 0 or 2.5 up to about 11 or 14.

In certain embodiments, the preferred pH of the composition containing no additional antimicrobial agents would be from about 0.01 to 6.

In certain embodiments, the pH adjusting and/or buffering agent is present in a total concentration of from about 0.01, 0.5, 1, 1.5, 2, 2.5, 3, 3.5, 5, or 7 wt. %, and up to about 15, 12, 10, 8, 6, 4, 2.2, 0.1, or 0.05 wt. %.

Nonionic Surfactants

Nonionic surfactants can be included to enhance the cleaning properties of the present solutions and/or to enhance solubility of ingredients contained therein.

Suitable nonionic surfactants include alkoxylated surfactants such as alkoxylates made from ethylene oxide (EO), propylene oxide (PO), and butylene oxide (BO). Suitable alkoxylated surfactants include homo or copolymers or terpolymers, capped EO/PO/BO copolymers, alcohol alkoxylates, capped alcohol alkoxylates, mixtures thereof, or the like. Suitable alkoxylated surfactants for use as solvents include EO/PO block copolymers, such as the Pluronic™ and reverse Pluronic surfactants; alcohol alkoxylates such as Dehypon™ LS-54, and Dehypon™ LS-36 capped alcohol alkoxylates, such as Plurafac™ LF221 and Tegoten™ EC11. More specifically, the composition of the present specification can include an alkoxylated primary or secondary alcohol having from 8 to 18 carbon atoms reacted with from 2 to 12 moles of ethylene, and/or propylene, and/or butylene oxide. In an embodiment, the nonionic surfactant has from 3 to 18 moles of alkylene oxide, in another embodiment from 3 to about 10 moles of ethylene oxide (EO), and in yet another embodiment about 7 moles of EO. Examples include lauryl alcohol ethoxylated with 3 moles of ethylene oxide (EO), coco alcohol ethoxylated with 3 moles EO, stearyl alcohol ethoxylated with 5 moles EO, mixed $C_{12}$-$C_{15}$ alcohol ethoxylated with 7 moles EO, mixed secondary $C_{11}$-$C_{15}$ alcohol ethoxylated with 7 moles EO, mixed $C_9$-$C_{11}$ linear alcohol ethoxylated with 6 moles EO and the like. In some embodiments, the nonionic surfactant can have from 8 to 15 carbon atoms in the alkyl group. In an embodiment, the composition comprises the alcohol alkoxylates, particularly the alcohol ethoxylates and propoxylates, especially the mixed ethoxylates and propoxylates, particularly with 3-7 oxyethylene (EO) units and 3-7 oxypropylene (PO) units such as the alcohol Dehypon™ available from Cognis Corporation, having 5 EO units and 4 PO units.

The semi-polar type of nonionic surface-active agents are another class of nonionic surfactant which may be used in compositions of the present specification. Semi-polar nonionic surfactants include the amine oxides (e.g. tertiary amine oxides), phosphine oxides, sulfoxides and their alkoxylated derivatives.

In certain embodiments, water soluble amine oxide surfactants are selected from the octyl, decyl, dodecyl, isododecyl, coconut, or tallow alkyl di-(lower alkyl) amine oxides, specific examples of which are octyldimethylamine oxide, nonyldimethylamine oxide, decyldimethylamine oxide, undecyldimethylamine oxide, dodecyldimethylamine oxide, iso-dodecyldimethyl amine oxide, tridecyldimethylamine oxide, tetradecyldimethylamine oxide, pentadecyldimethylamine oxide, hexadecyldimethylamine oxide, heptadecyldimethylamine oxide, octadecyldimethylamine oxide, dodecyldipropylamine oxide, tetradecyldipropylamine oxide, hexadecyldipropylamine oxide, tetradecyldibutylamine oxide, octadecyldibutylamine oxide, bis(2-hydroxyethyl)dodecylamine oxide, bis(2-hydroxyethyl)-3-dodecoxy-1-hydroxypropylamine oxide, dimethyl-(2-hydroxydodecyl)amine oxide, 3,6,9-trioctadecyldimethylamine oxide and 3-dodecoxy-2-hydroxypropyldi-(2-hydroxyethyl)amine oxide.

When used, in certain embodiments, the concentration of the nonionic surfactant can be from about 0.02, 0.1, 1, 5, 10, or 20 wt. %, and up to about 30, 25, 15, 8, 3, or 0.5 wt. %.

Anionic Surfactants

Anionic surfactants aid in providing cleaning power boost when used in solutions and some also contribute to antimicrobial efficacy of the overall composition. Certain classes of anionic surfactants such as, without limitation, alkylbenzenesulfonic acids, alkyldiphenyloxide disulfonates, alkyl sulfates, alkyl sulfonates, alkyl phosphate esters, and salts thereof can also act as antimicrobial agents. Anionic surfactants that can be used in the present compositions include sulfates, such as alkyl ether sulfates, alkyl sulfates, the linear and branched primary and secondary alkyl sulfates, alkyl ethoxysulfates, fatty oleyl glycerol sulfates, alkyl phenol ethylene oxide ether sulfates, glucamine sulfates, and sulfates of alkylpolysaccharides such as the sulfates of alkylpolyglucoside, alkyl poly(ethyleneoxy) ether sulfates and aromatic poly(ethyleneoxy) sulfates such as the sulfates or condensation products of ethylene oxide and nonyl phenol (usually having 1 to 6 oxyethylene groups per molecule).

Anionic sulfonate surfactants that can be used include alkyl sulfonates, the linear and branched primary and secondary alkyl sulfonates, sulfate esters, sulfonate esters, the aromatic sulfonates with or without substituents, including alkylbenzene sulfonates, and their salts.

Anionic carboxylate surfactants can also be used such as alkyl carboxylic acids (and salts), such as alkanoic acids (and alkanoates), ester carboxylic acids (e.g. alkyl succinates), ether carboxylic acids, and the like. Such carboxylates include alkyl ethoxy carboxylates, alkyl aryl ethoxy carboxylates, alkyl polyethoxy polycarboxylate surfactants and soaps (e.g. alkyl carboxyls). Secondary carboxylates useful in the present compositions include those which contain a carboxyl unit connected to a secondary carbon. The secondary carbon can be in a ring structure, e.g. as in p-octyl benzoic acid, or as in alkyl-substituted cyclohexyl carboxylates. The secondary carboxylate surfactants typically contain no ether linkages, no ester linkages and no hydroxyl groups. Further, they typically lack nitrogen atoms in the head-group (amphiphilic portion). Suitable secondary soap surfactants typically contain 11-13 total carbon atoms, although more carbons atoms (e.g., up to 16) can be present. Suitable carboxylates also include acylamino acids (and salts), such as acylglutamates, acyl peptides, taurates (e.g. N-acyl taurates and fatty acid amides of methyl tauride), and the like.

Preferred anionic surfactants include $C_6$-$C_{24}$ alkylbenzene sulfonates; alkyl sarcosines and their salts, $C_6$-$C_{24}$ olefin sulfonates, $C_6$-$C_{24}$ paraffin sulfonates, cumene sulfonate, xylene sulfonate; $C_6$-$C_{24}$ alcohol sulfates (preferably $C_6$-$C_{12}$ alcohol sulfates), and $C_6$-$C_{24}$ alcohol ether sulfates having 1 to about 20 ethylene oxide groups. Other suitable anionic surfactants include alkyl phosphonates, alkyl ether phosphonates, alkyl phosphates, alkyl ether phosphates, and phosphate esters.

When used, in certain embodiments, the concentration of the anionic or nonionic surfactant(s) can be from about 0.02, 0.1, 0.2, 0.4, 0.8, 1, 2.5, 5, 6.5, 10, or 20 wt. %, and up to about 40, 30, 25, 20, 15, 8, 3, or 0.5 wt. %.

Hydrotropes

In certain embodiments, the solution or composition of the invention may include one or more hydrotropes for improving solubility and phase stability, such as salts of aryl and alkylaryl sulfonic acids such as xylene sulfonic acid, cumene sulfonic acid, and toluene sulfonic acid. Other hydrotropes include polyether phosphate esters, alkyl sulfates, alkyl and alkylaryl sulfonates, diphenyloxide disulfonates, and benzoic acid salts.

When used, in certain embodiments, the hydrotrope can be present in a concentration of from about 0.1, 1, 3, 5, 10, or 20 wt. % and up to about 25, 15, 8, 4, or 1.5 wt. %.

It will be appreciated that certain hydrotropes can also be categorized as anionic or nonionic surfactants. The skilled person will appreciate the various categories to which the same compound can belong.

Skin Conditioning Agents

In embodiments for use on skin, the solution may include an effective amount of at least one emollient, humectant or other skin conditioning agent, including but not limited to glycerin, polyglycerin, butylene glycol, glycerides, castor oil, allantoin, cationic polymers, lanolin and its derivatives, polyols and glycols such as glycerol, polyglycerol, sorbitol, mannitol, erythritol, xylitol, arabitol, ribitol, dulcitol, lactitol, maltitol, propylene glycol, hexylene glycol, ceramides, essential fatty acids such as linolenic acid, gamma-linolenic acid, linoleic acid, gamma-linoleic acid, tocopherols such as tocopheryl acetate, quaternised gums, quaternised polymers, glucose-ethers, vegetable oils, long chain fatty acids, long chain alcohols (e.g. cetyl alcohol), and phospholipids, and mineral oils.

When used, in certain embodiments, the skin conditioning agent can be present in a concentration of from about 0.01, 0.5, 2, 5, or 10 wt. %, and up to about 30, 25, 20, 15, 8, 4, or 1 wt. %.

Other Ingredients

The present compositions can also include other ingredients such as anti-foaming agents, e.g. siloxanes, low-solubility oils, and low-HLB nonionic surfactants. In certain embodiments the other ingredients are in a concentration of from about 0.001, 0.1, 0.5, 2, 4, 5, or 7 wt. %, and up to about 10, 8, 5, 4, or 3 wt. %.

In certain embodiments, builders can be present in a concentration of from about 0.01, 0.5, 2, 4, or 5 wt. %, and up to about 8, 3, 1, or 0.1 wt. %.

In certain embodiments, soil suspenders can be present in a concentration of from about 0.01, 0.5, 2, 5, or 10 wt. %, and up to about 15, 8, 4, 1, or 0.1 wt. %.

In certain embodiments, brighteners can be present in a concentration of from about 0.0005, 0.05, 0.1, 2, or 7 wt. %, and up to about 10, 5, 3, 1, or 0.01 wt. %.

In certain embodiments, radical scavengers and antioxidants can be present in a concentration of from about 0.005, 0.5, 1, or 5 wt. %, and up to about 15, 10, 3, 0.1, or 0.01 wt. %.

In certain embodiments, the present compositions are essentially free of compounds such as N methyl-gamma-butyrolactam (NMP), N-ethyl-gamma-butyrolactam (NEP), halogen compounds, such as compounds containing chlorine and bromine (e.g. chloroacetamide), glycosylated mucocidin antimicrobial peptides, and known antibiotics such as erythromycin.

The invention is further described by the following non-limiting examples.

EXPERIMENTS AND TEST RESULTS

A number of solutions were prepared using the ingredients summarized in Table A and tested for their antimicrobial activity. The solutions and antimicrobial test results are summarized in Tables 1.0 to 4.0 (below). In these tables, the actual active concentration of each ingredient in terms of wt. % is shown.

TABLE A

| Molecule | Classification | Commercial Name (Manufacturer) | Active Content |
|---|---|---|---|
| Acetic acid | Antimicrobial agent; Carboxylic acid; Acidic pH adjusting agent | Glacial acetic acid (Sigma) | 100% |
| C8-C10 alkoxylated phosphate esters | Antimicrobial agent; Anionic surfactant | Multitrope ™ 1214 (Croda) | 100% |
| C9-C14 alkyl benzenesulfonic acids | Antimicrobial agent; Anionic surfactant | Bio-Soft ™ S-101 LS (Stepan) | >98% |
| Alkyl(C10-C16)benzenesulfonic acid | Antimicrobial agent; Anionic surfactant | Bio-Soft ™ S-101 (Stepan) | 95.50% |
| Alkyldimethylbenzylammonium chloride (ADBAC) | Antimicrobial agent; Quaternary ammonium compound; Cationic surfactant | BTC ™ 50 (Stepan) | 50% |
| Benzyl alcohol | Antimicrobial agent; Monohydroxy Alcohol Solvent | Benzyl alcohol (Univar) | 95-100% |
| Butyl-3-hydroxy butyrate | Solvent | Omnia ™ solvent (Eastman) | >98% |
| C9-C11 ethoxylated alcohols | Nonionic surfactant | Tomadol ™ 91-6 (Evonic) | 100% |

TABLE A-continued

| Molecule | Classification | Commercial Name (Manufacturer) | Active Content |
|---|---|---|---|
| Calcium hypochlorite | Antimicrobial agent; Chlorine compound | Calcium Hypochlorite (Sigma) | 100% |
| Capryleth-9 carboxylic acid | Antimicrobial agent; Anionic surfactant | Akypo™ LF 2 (Kao Chemicals) | >85% |
| Chlorhexidine gluconate | Antimicrobial agent | Chlorhexidine gluconate 20% (VWR) | 20% |
| Citric acid | Antimicrobial agent; Carboxylic acid; Acidic pH adjusting agent; buffering agent | Anhydrous citric acid (Brenntag) | 95-100% |
| Cyanuric acid | Triazine; Chelating agent | Cyanuric acid (Sigma) | 100% |
| Didecyldimethylammonium chloride (DDAC)/ADBAC | Antimicrobial agent; Quaternary ammonium compound mixture; compound; Cationic surfactant | BTC™ 1210 (Stepan) | 79-83% |
| Dimethyl succinate | Antimicrobial agent; Dibasic ester solvent | Dimethyl succinate (Sigma) | 100% |
| Dimethylol propionic acid | Antimicrobial agent; Carboxylic acid; Acidic pH adjusting agent | 2,2-Bis(hydroxymethyl)propionic acid (Sigma) | 100% |
| Ethanol | Antimicrobial agent; Monohydroxy Alcohol Solvent | Ethyl alcohol (VWR) | 100% |
| Ethylhexylglycerin | Antimicrobial agent; Glycerol ether | Sensiva™ SC 50 (Schulke) | >95% |
| Etidronic acid | Chelating agent; Acidic pH adjusting agent; buffering agent | Dequest™ 2010 (Italmach) | 60% |
| 2-Furoic acid | Antimicrobial agent; Cyclic carboxylic acid | 2-furoic acid (Sigma) | 100% |
| Gallic acid | Antimicrobial agent; Cyclic carboxylic acid | Gallic acid (Derbiotech) | >98% |
| Glutaraldehyde | Antimicrobial agent; Aldehyde | Glutaraldehyde solution (Sigma) | 25% |
| Isopropanol | Antimicrobial agent; Monohydroxy Alcohol Solvent | Isopropyl alcohol (VWR) | 100% |
| Lactic acid | Antimicrobial agent; Carboxylic acid | Lactic acid (Sigma) | 80-90% |
| Lauramine oxide | Antimicrobial agent; Amphoteric surfactant | Ammonyx™ LO (Stepan) | 30% |
| Malic acid | Antimicrobial agent; Carboxylic acid | Malic acid (Tate & Lyle) | >95% |
| Mandelic acid | Antimicrobial agent; Cyclic carboxylic acid | Mandelic acid (Sigma) | 100% |
| Methyl methoxy benzoate | Antimicrobial agent; Ester; Fragrance | Methyl 2-methoxybenzoate (Sigma) | 100% |
| N,N-dimethyl 9-decenamide | Antimicrobial agent; Organic amide | Steposol™ Met-10U (Stepan) | 90-100% |
| N,N-dimethylalkylamide (C8-C10) | Antimicrobial agent; Organic amide | Steposol™ M-8-10 | 70-99% |
| N-butyl-gamma-butyrolactam | Antimicrobial agent; Solvent | Tamisolve™ NxG (Eastman) | >99.5% |
| N-octyl-gamma-butyrolactam | Nonionic Surfactant; Film forming agent | Surfadone™ LP-100 (Ashland) | >98% |
| Phosphoric acid | Antimicrobial agent; Mineral acid; Acidic pH adjusting agent; buffering agent | Phosphoric acid FG (Brenntag) | 75% |
| Picolinic acid | Antimicrobial agent; Cyclic carboxylic acid; Chelating agent | pyridine-2,6-dicarboxylic (Alfa Aesar) | 95-100% |
| Potassium hydroxide (KOH) | Alkaline pH adjusting agent | Potassium hydroxide NF (Univar) | 45% |
| Salicylic acid | Antimicrobial agent; Cyclic carboxylic acid | Salicylic acid USP (Colombus) | >99% |
| Sodium capryloyl glutamate | Antimicrobial agent; Anionic surfactant | Plantapon™ ACG HC (BASF) | 50% |
| Sodium cocoyl isothionate | Antimicrobial agent; Anionic surfactant | Hostapon™ SCI 85 P (Clariant) | 85% |
| Sodium laureth sulfosuccinate | Antimicrobial agent; Anionic surfactant | Texapon™ SB 3 KC (BASF) | 31-35% |
| Sodium lauroyl sarcosinate | Antimicrobial agent; Anionic surfactant | N-Lauroylsarcosine sodium salt (Sigma) | 100% |

Example 1

TABLE 1.0

| Ingredient | Solution A | Solution B | Solution AA |
|---|---|---|---|
| N-butyl-gamma-butyrolactam | 4 | 7 | — |
| N-octyl-gamma-butyrolactam | — | — | 1 |
| C9-C11 ethoxylated alcohols | — | — | 2.2 |
| Deionized water | q.s. to 100 | q.s. to 100 | q.s. to 100 |
| $Log_{10}$ Reduction of *M. smegmatis*, 5 minutes contact time | 1.23 | 1.61 | 0 |
| $Log_{10}$ Reduction of *M. smegmatis*, 75 seconds contact time | Not tested | 0.11 | Not tested |

Solutions A, B and AA were prepared to test the antimicrobial activity of N-alkyl-gamma-butyrolactam, specifically N-butyl-gamma-butyrolactam and N-octyl-gamma-butyrolactam. These solutions were tested using the ASTM E2197-02 test method (5-minute contact time or 75 second contact time) without soil load, against hard-to-kill mycobacteria (*M. smegmatis*). The $log_{10}$ reductions in mycobacteria at a 5-minute contact time is shown in the second last row and demonstrate that N-butyl-gamma-butyrolactam surprisingly possesses antimicrobial activity, even against hard-to-kill mycobacteria. On the other hand, N-octyl-gamma-butyrolactam (Solution AA) possesses no antimicrobial activity under these test conditions. It is expected, based on these results, that N-alkyl-gamma-butyrolactams with an alkyl chain length greater than C6 will be ineffective in inactivating hard-to-kill microbes such as mycobacteria.

Solution B was also tested using ASTM E2197-02 test method (75 second contact time), without soil load, against mycobacteria (*M. smegmatis*) and achieved a $log_{10}$ reduction of 0.11 (shown in the last row of Table 1.0). This result can be compared with the results for the solutions in EXAMPLE 2 below to highlight the synergistic boost in antimicrobial efficacy of solution containing N-butyl-gamma-butyrolactam and an additional antimicrobial agent.

Example 2

Additional solutions were prepared to assess the antimicrobial activity of N-alkyl-gamma-butyrolactam, specifically N-butyl-gamma-butyrolactam, when combined with other antimicrobial agents in aqueous solution. These solutions are summarized in Tables 2.0, 2.1, and 2.2 below and tested using ASTM E2197-02 test method (75 second contact time), without soil load, against mycobacteria (*M. smegmatis*).

TABLE 2.0

| Ingredient | C | C1 | D | D1 | E | E1 | F | F1 |
|---|---|---|---|---|---|---|---|---|
| N-butyl-gamma-butyrolactam | — | 7 | — | 7 | — | 7 | — | 7 |
| Citric acid | 3 | 3 | — | — | — | — | — | — |
| Acetic acid | — | — | 5 | 5 | — | — | — | — |
| 2-Furoic acid | — | — | — | — | 0.5 | 0.5 | — | — |
| Alkyl (C10-C16) benzenesulfonic acid | — | — | — | — | — | — | 0.5 | 0.5 |
| Deionized water | q.s. to 100 | q.s. to 100 | q.s. to 100 | q.s. to 100 | q.s. to 100 | q.s. to 100 | q.s. to 100 | q.s. to 100 |
| $Log_{10}$ Reduction of *M. smegmatis*, 75 seconds contact time | 0.00 | 1.98 | 1.16 | 1.78 | 1.85 | 3.57 | 0.27 | 1.54 |

Solutions C, C1, D, D1, E, E1, F, and F1 contain different concentrations of antimicrobial carboxylic acids (citric acid, acetic acid, 2-furoic acid) or alkylbenzene sulfonic acid in aqueous solution. Solutions C1, D1, E1, and F1 also contain 7 wt. % N-butyl-gamma-butyrolactam. The results (when compared with the result for Solution B in Table 1.0), show a synergy between N-butyl-gamma-butyrolactam and the additives used in Table 2.0.

TABLE 2.1

| Ingredient | G | G1 | H | H1 | I | I1 |
|---|---|---|---|---|---|---|
| N-butyl-gamma-butyrolactam | — | 7 | — | 7 | — | 7 |
| Isopropanol | 25 | 25 | — | — | — | — |
| Ethanol | — | — | 25 | 25 | — | — |
| Dodecyldimethylammonium chloride (DDAC)/ADBAC | — | — | — | — | 0.3 | 0.3 |
| Potassium hydroxide (KOH) | — | — | — | — | pH to 11 | pH to 11 |
| Deionized water | q.s. to 100 | q.s. to 100 | q.s. to 100 | q.s. to 100 | q.s. to 100 | q.s. to 100 |
| $Log_{10}$ Reduction of *M. smegmatis*, 75 seconds contact time | 0.00 | 0.65 | 0.00 | 0.99 | 0.03 | 0.47 |

Solutions G to I1 contain different antimicrobial agents in aqueous solution. The desired pH of 11 for Solutions I and I1 was achieved using KOH. The pH of the other solutions was not measured. Solutions G1, H1, and I1 also contain 7 wt. % N-butyl-gamma-butyrolactam. The results (when compared with the result for Solution B in Table 1.0) show a synergy between N-butyl-gamma-butyrolactam and each additional antimicrobial agent used in Table 2.1.

TABLE 2.2

| Ingredient | Solution | | | |
|---|---|---|---|---|
| | J | J1 | K | K1 |
| N-butyl-gamma-butyrolactam | — | 7 | — | 7 |
| Calcium hypochlorite | 0.2 | 0.2 | — | — |
| DDAC and glutaraldehyde (1:1 ratio) | — | — | 0.4 | 0.4 |
| Potassium hydroxide (KOH) | pH to 11 | pH to 11 | Not measured | Not measured |
| Deionized water | q.s. to 100 | q.s. to 100 | q.s. to 100 | q.s. to 100 |

TABLE 2.2-continued

| Ingredient | Solution | | | |
|---|---|---|---|---|
| | J | J1 | K | K1 |
| $Log_{10}$ Reduction of *M. smegmatis*, 75 seconds contact time | 0.60 | 0.78 | 0.18 | 0.39 |

Solutions J, J1, K, and K1 contain an antimicrobial agent selected from calcium hypochlorite and DBAC/glutaraldehyde. Solutions J1 and K1 also contain 7 wt. % N-butyl-gamma-butyrolactam. The results (when compared with the result for Solution B in Table 1.0) show a synergy between N-butyl-gamma-butyrolactam and each of the antimicrobial agents used in Table 2.2.

Example 3

The 75 second contact time used in EXAMPLE 2 was selected to resemble conditions in which rapid evaporation of the solution may occur following application to a surface to be disinfected. The inventor has found that the synergy is still present, and an increase in microbial reduction is achieved, following an increase in contact time to 80 or 160 seconds, as shown in Tables 3.0-3.2, below, which list additional solutions containing N-butyl-gamma-butyrolactam and at least one additional antimicrobial agent.

TABLE 3.0

| Solutions | M | M1 | N | N1 | O | O1 | P | P1 | Q | Q1 | R | R1 | S | S1 | T | T1 |
|---|---|---|---|---|---|---|---|---|---|---|---|---|---|---|---|---|
| N-butyl-gamma-butyrolactam | 7.0 | — | 7.0 | — | 7.0 | — | 7.0 | — | 7.0 | — | 7.0 | — | 7.0 | — | 7.0 | — |
| C9-C11 ethoxylated alcohols | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 | 0.1 |
| Salicylic acid | 0.2 | 0.2 | — | — | — | — | — | — | — | — | — | — | — | — | — | — |
| Benzyl alcohol | — | — | 0.8 | 0.8 | — | — | — | — | — | — | — | — | — | — | — | — |
| Dimethyl succinate | — | — | — | — | 5.0 | 5.0 | — | — | — | — | — | — | — | — | — | — |
| Picolinic acid | — | — | — | — | — | — | 0.2 | 0.2 | — | — | — | — | — | — | — | — |
| Cyanuric acid | — | — | — | — | — | — | — | — | 0.2 | 0.2 | — | — | — | — | — | — |
| Mandelic acid | — | — | — | — | — | — | — | — | — | — | 0.4 | 0.4 | — | — | — | — |
| Dimethylol propionic acid | — | — | — | — | — | — | — | — | — | — | — | — | 0.4 | 0.4 | — | — |
| Gallic acid | — | — | — | — | — | — | — | — | — | — | — | — | — | — | 0.4 | 0.4 |
| Deionized water | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 |
| Potassium hydroxide or phosphoric acid | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 |
| $Log_{10}$ Reduction of *M. smegmatis*, 80 seconds contact time | 0.43 | — | 0.67 | — | 0.82 | — | 0.48 | — | 0.41 | — | 0.56 | — | 0.37 | — | 0.24 | — |
| $Log_{10}$ Reduction of *M. smegmatis*, 160 seconds contact time | 1.03 | 0.31 | 2.16 | 0.23 | 2.61 | 0.39 | 1.00 | 0.00 | 0.72 | 0.00 | 0.95 | 0.24 | 0.78 | 0.12 | 0.79 | 0.09 |

TABLE 3.1

| Solutions | U | U1 | V | V1 | W | W1 | X | X1 | Y | Y1 | Z | Z1 |
|---|---|---|---|---|---|---|---|---|---|---|---|---|
| N-butyl-gamma-butyrolactam | 7 | — | 7 | — | 7 | — | 7 | — | 7 | — | 7 | — |
| C9-C11 ethoxylated alcohols | 0.1 | 0.1 | 0.1 | 0.1 | 0.1 | 0.1 | 0.1 | 0.1 | 0.1 | 0.1 | 0.1 | 0.1 |
| Malic acid | 0.40 | 0.40 | — | — | — | — | — | — | — | — | — | — |
| Lactic acid | — | — | 0.40 | 0.4 | — | — | — | — | — | — | — | — |
| Methyl methoxy benzoate | — | — | — | — | 0.40 | 0.40 | — | — | — | — | — | — |
| Capryleth-9 carboxylic acid | — | — | — | — | — | — | 0.23 | 0.23 | — | — | — | — |
| Sodium lauroyl sarcosinate | — | — | — | — | — | — | — | — | 0.15 | 0.15 | — | — |
| Butyl-3-hydroxy butyrate | — | — | — | — | — | — | — | — | — | — | 0.80 | 0.80 |
| Deionized water | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 |
| Potassium hydroxide or phosphoric acid | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 |
| $Log_{10}$ Reduction of *M. smegmatis*, 80 seconds contact time | 0.44 | — | 0.47 | — | 0.67 | — | 0.46 | — | 0.55 | — | 0.60 | — |
| $Log_{10}$ Reduction of *M. smegmatis*, 160 seconds contact time | 1.31 | 0.19 | 1.10 | 0.22 | 0.94 | 0.00 | 0.75 | 0.14 | 0.91 | 0.06 | 0.93 | 0.06 |

TABLE 3.2

| Solutions | AA | AA1 | BB | BB1 | CC | CC1 | DD | DD1 | EE | EE1 |
|---|---|---|---|---|---|---|---|---|---|---|
| N-butyl-gamma-butyrolactam | 7 | — | 7 | — | 7 | — | 7 | — | 7 | — |
| C9-C11 ethoxylated alcohols | 0.1 | 0.1 | 0.1 | 0.1 | 0.1 | 0.1 | 0.1 | 0.1 | 0.1 | 0.1 |
| Ethylhexylglycerin | 0.30 | 0.30 | — | — | — | — | — | — | — | — |
| Acetic acid | — | — | 1.50 | 1.50 | — | — | — | — | — | — |
| N,N-dimethylalkylamide (C8-C10) | — | — | — | — | 0.30 | 0.30 | — | — | — | — |
| N,N-dimethyl 9-decenamide | — | — | — | — | — | — | 0.30 | 0.30 | — | — |
| Deionized water | q.s. to 100 | q.s. to 100 | q.s. to 100 | q.s. to 100 | q.s. to 100 | q.s. to 100 | q.s. to 100 | q.s. to 100 | q.s. to 100 | q.s. to 100 |
| Potassium hydroxide or phosphoric acid | pH to 2.5 | pH to 2.5 | pH to 2.5 | pH to 2.5 | pH to 2.5 | pH to 2.5 | pH to 2.5 | pH to 2.5 | pH to 2.5 | pH to 2.5 |
| $Log_{10}$ Reduction of *M. smegmatis*, 80 seconds contact time | — | — | — | — | — | — | — | — | 0.39 | — |
| $Log_{10}$ Reduction of *M. smegmatis*, 160 seconds contact time | 1.97 | 0.28 | 1.71 | 0.26 | 1.59 | 0.18 | 1.62 | 0.18 | 0.46 | 0.00 |

Solutions M through EE1 were prepared and tested using the ASTM E2197-02 test method, with soil load, against *mycobacterium M. smegmatis*. Contact times of 80 or 160 seconds were employed as shown above. Solution EE contains $C_9$-$C_{11}$ ethoxylated alcohols (0.1 wt. %) and N-butyl-gamma-butyrolactam (7 wt. %). Phosphoric acid was added to achieve pH 2.5. Solution EE1 is the same as solution EE except that N-butyl-gamma-butyrolactam is absent. The results for Solution EE1 show that the $C_9$-$C_{11}$ ethoxylated alcohols (0.1 wt. %) do not contribute to antimicrobial efficacy. Comparing the results for Solution EE to the results for the other solutions M through to DD1 shows that the addition of N-butyl-gamma-butyrolactam leads to a synergistic boost in antimicrobial activity of all the solutions.

Example 4

Additional solutions were prepared similar to those shown in Tables 2.0 to 2.2, where each aqueous solution contained more than one known active ingredient, either with or without a N-alkyl-gamma-butyrolactam.

TABLE 4.0

| Solution: | Mixture of antimicrobial actives: | Antimicrobial synergy when combined with N-butyl-gamma-butyrolactam: |
|---|---|---|
| #1 | Citric acid (0.5 wt. %) + C9-C14 alkyl benzenesulfonic acids (0.25 wt. %) | Yes |
| #2 | DDAC (0.3 wt. %) + Isopropanol (32 wt. %) | Yes |
| #3 | Salicylic acid (0.3 wt. %) + Ethanol (35 wt. %) | Yes |
| #4 | Mandelic acid (0.6 wt. %) + 2-Furoic acid (0.6 wt. %) | Yes |
| #5 | DDAC (0.24 wt. %) + Glutaraldehyde (0.2 wt. %) + Chlorhexidine gluconate (0.2 wt. %) | Yes |

As shown in Table 4, similar observations were made where the addition of a N-alkyl-gamma-butyrolactam solvent, more specifically N-butyl-gamma-butyrolactam, led to a synergistic boost in the overall antimicrobial activity of each solution containing more than one known antimicrobial active ingredient. In the above solutions, the concentrations shown are actual active concentrations.

Example 5

Additional non-limiting exemplary solutions were prepared and are displayed below. In these solutions, the concentrations shown below are actual active concentrations.

Disinfectant Concentrate
N-butyl-gamma-butyrolactam (45.0 wt. %)
mixture of C9-C14 alkyl benzenesulfonic acids (8.0 wt. %)
Salicylic acid (3.5 wt. %)
deionized water (q.s. to 100)
pH: 0.7
Ready-to-Use Topical Disinfectant Solution
N-butyl-gamma-butyrolactam (6.0 wt. %)
sodium capryloyl glutamate (2.0 wt. %)
sodium cocoyl isethionate (1.8 wt. %)
sodium lauroyl sarcosinate (0.2 wt. %)
deionized water (q.s. to 100)
pH: 3.6 (adjusted using citric acid)
Ready-to-Use Hard Surface Sanitizer
N-butyl-gamma-butyrolactam (5.0 wt. %)
laurylamine oxide (1.0 wt. %)
deionized water (q.s. to 100)
pH: 2.6 (adjusted using phosphoric acid)
Ready-to-Use Hard Surface Disinfectant
N-butyl-gamma-butyrolactam (7.0 wt. %)
C8-C10 alkoxylated phosphate esters (0.4 wt. %)
mixture of C9-C14 alkyl benzenesulfonic acids (0.2 wt. %)
C9-C11 ethoxylated alcohols (0.15 wt. %)
etidronic acid (0.2 wt. %)
deionized water (q.s. to 100)
pH: 2.3
Antimicrobial Hand Soap Solution
N-butyl-gamma-butyrolactam (6.2 wt. %)
capryleth-9 carboxylic acid (3.0 wt. %)
disodium laureth sulfosuccinate (1.2 wt. %)
ethanol (28.0 wt. %)
salicylic acid (0.25 wt. %)
deionized water (q.s. to 100)
pH: 2.8

The foregoing description of embodiments is by way of example only and is not intended to limit the scope of the invention as herein described and claimed.

The invention claimed is:

1. A ready-to-use antimicrobial composition comprising:
   (a) a synergistic combination of antimicrobial agents, and
   (b) a diluent, wherein the antimicrobial agents in the antimicrobial composition consist of:
      (i) about 0.5 wt. % to about 16 wt. % of a first antimicrobial agent consisting of at least one compound according to Formula 1:

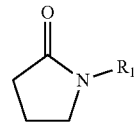

[Formula 1]

wherein $R_1$ is a branched or unbranched, saturated or unsaturated, unsubstituted C3 to C5 alkyl chain or a C3 alkyl chain substituted with a methoxy group;
   (ii) an effective amount of at least 0.05 wt. % to about 15 wt. % of at least one second antimicrobial agent selected from the group consisting of salicylic acid, 2-furoic acid, mandelic acid, acetic acid, dimethylol propionic acid, gallic acid, malic acid, lactic acid, and salts thereof; and
   (iii) optionally, an effective amount of at least one additional antimicrobial agent selected from the group consisting of carboxylic acids and salts thereof other than those in (ii), alcohols, anionic surfactants, amphoteric surfactants, quaternary ammonium compounds, phenols, aldehydes, biguanides, mineral acids, glycerol ethers, antimicrobial solvents, and antimicrobial metals;
   wherein the diluent is present at q.s. to 100; and
   wherein the antimicrobial composition is substantially free of peroxygen compounds, antibiotics, N-methyl pyrrolidone (NMP), N-ethyl pyrrolidone (NEP), and chloroacetamide.

2. The antimicrobial composition of claim 1, wherein said first antimicrobial agent is a C4 N-alkyl-gamma-butyrolactam.

3. The antimicrobial composition of claim 1, wherein said at least one compound according to Formula 1 is selected from the group consisting of N-butyl-gamma-butyrolactam, N-isobutyl-gamma-butyrolactam, and N-methoxypropyl-gamma-butyrolactam.

4. The antimicrobial composition of claim 1, wherein said diluent is water.

5. The antimicrobial composition of claim 1, wherein the at least one additional antimicrobial agent is selected from the group consisting of said carboxylic acids and salts thereof other than those in (ii).

6. The antimicrobial composition of claim 5, wherein the at least one additional antimicrobial agent is selected from the group consisting of citric acid, glycolic acid, benzoic acid, sulfosuccinic acid, propionic acid, oxalic acid, and salts thereof.

7. The antimicrobial composition of claim 1, wherein the at least one additional antimicrobial agent is selected from the group consisting of anionic surfactants, amphoteric surfactants, quaternary ammonium compounds, and antimicrobial solvents.

8. The antimicrobial composition of claim 1, further comprising at least one non-antimicrobial solvent.

9. The antimicrobial composition of claim 1, further comprising at least one ingredient selected from the group consisting of stabilizing agents, buffering agents, nonionic surfactants, cationic surfactants, hydrotropes, skin conditioning agents, anti-foaming agents, builders, soil suspenders, anti-redeposition agents, brightening agents, radical scavengers, dyes, fragrances, rheology modifiers, emulsifiers, corrosion inhibitors, softening agents, anti-static agents, anti-wrinkling agents, dye transfer inhibition agents, color protection agents, odor removal agents, odor capturing agents, soil shielding agents, soil releasing agents, ultraviolet light protection agents, water repellency agents, insect repellency agents, anti-pilling agents, souring agents, mildew removing agents, film-forming agents, plasticizers, and allergicides.

10. A method of reducing a microbial load on a surface, the method comprising, (a) identifying a surface in need of microbial reduction, and (b) applying an effective amount of the antimicrobial composition according to claim 1 to the surface for a time sufficient to reduce the number of microbes on the surface by at least 50%.

11. The method of claim 10, wherein the microbes are selected from the group consisting of bacteria, viruses, fungi, yeasts, mycobacteria, fungal spores, bacterial spores, viroids, phages, prions, protozoa, parasites, and combinations thereof.

12. The method of claim 11, wherein the microbes are selected from the group consisting of mycobacteria, yeast, bacteria, and combinations thereof.

13. The antimicrobial composition of claim 1, wherein the antimicrobial solvents are selected from the group consisting of C1-C8 alcohols, cyclic alcohols, dibasic esters, and ethylhexylglycerin.

14. The antimicrobial composition of claim 13, wherein the antimicrobial solvents are selected from the group consisting of ethanol, propanol, butanol, phenethyl alcohol, isopropyl alcohol, benzyl alcohol, phenoxyethanol, dimethyl adipate, dimethyl succinate, and ethylhexylglycerin.

15. The antimicrobial composition of claim 7, wherein the at least one additional antimicrobial agent is selected from the group consisting of said anionic surfactants.

16. The antimicrobial composition of claim 1, wherein the at least one second antimicrobial agent is selected from the group consisting of 2-furoic acid, salicylic acid, mandelic acid, and salts thereof.

17. The antimicrobial composition of claim 9, wherein said at least one ingredient is selected from the group consisting of buffering agents, nonionic surfactants, skin conditioning agents, hydrotropes, and corrosion inhibitors.

18. The antimicrobial composition of claim 1, further comprising at least one non-antimicrobial solvent selected from the group consisting of butyl 3-hydroxybutyrate and glycol ethers.

19. The antimicrobial composition of claim 4, further comprising an effective amount of a pH adjusting agent.

20. The antimicrobial composition of claim 5, wherein the at least one additional antimicrobial agent is selected from the group consisting of sulfosalicylic acid, formic acid, butanoic, pentanoic acid, hexanoic acid, heptanoic acid, octanoic acid, nonanoic acid, decanoic acid, undecanoic acid, dodecanoic acid, maleic acid, ascorbic acid, alpha-or-beta hydroxy-acetic acid, neopentanoic acid, neoheptanoic acid, neodecanoic acid, malonic acid, succinic acid, glutaric acid, adipic acid, pimelic acid, suberic acid, and salts thereof.

21. A concentrated antimicrobial composition which, when combined with an effective amount of water, provides a ready-to-use composition comprising:
(a) a synergistic combination of antimicrobial agents, wherein the antimicrobial agents consist of:
(i) about 0.5 wt. % to about 16 wt. % of a first antimicrobial agent consisting of at least one compound according to Formula 1:

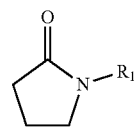

[Formula 1]

wherein $R_1$ is a branched or unbranched, saturated or unsaturated, unsubstituted C3 to C5 alkyl chain or a C3 alkyl chain substituted with a methoxy group;
(ii) an effective amount of at least 0.05 wt. % to about 15 wt. % of at least one second antimicrobial agent selected from the group consisting of salicylic acid, 2-furoic acid, mandelic acid, acetic acid, dimethylol propionic acid, gallic acid, malic acid, lactic acid, and salts thereof; and
(iii) optionally, an effective amount of at least one additional antimicrobial agent selected from the group consisting of carboxylic acids and salts thereof other than those in (ii), alcohols, anionic surfactants, amphoteric surfactants, quaternary ammonium compounds, phenols, aldehydes, biguanides, mineral acids, glycerol ethers, antimicrobial solvents, and antimicrobial metals; and
(b) water q.s. to 100;
wherein the antimicrobial composition is substantially free of peroxygen compounds, antibiotics, N-methyl pyrrolidone (NMP), N-ethyl pyrrolidone (NEP), and chloroacetamide.

* * * * *